US011672900B2

(12) United States Patent
Peri et al.

(10) Patent No.: US 11,672,900 B2
(45) Date of Patent: Jun. 13, 2023

(54) DETECTION OF BUBBLES IN IRRIGATION FLUID

(71) Applicant: BIOSENSE WEBSTER (ISRAEL) LTD., Yokneam (IL)

(72) Inventors: Eitan Peri, Givat Ada (IL); Alaa Zoabi, Kfar Masser (IL); Lior Botzer, Timrat (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 341 days.

(21) Appl. No.: 17/072,643

(22) Filed: Oct. 16, 2020

(65) Prior Publication Data

US 2021/0030974 A1 Feb. 4, 2021

Related U.S. Application Data

(62) Division of application No. 15/677,522, filed on Aug. 15, 2017, now Pat. No. 10,842,950.

(51) Int. Cl.
*A61M 3/02* (2006.01)
*A61M 5/36* (2006.01)
*A61B 18/00* (2006.01)
*G01F 1/688* (2006.01)
*G01F 1/74* (2006.01)

(52) U.S. Cl.
CPC ........ *A61M 3/0204* (2014.02); *A61M 3/0202* (2021.05); *A61M 3/0254* (2013.01); *A61M 5/365* (2013.01); *A61B 2018/00898* (2013.01); *A61B 2218/002* (2013.01); *A61M 2205/3368* (2013.01); *A61M 2205/50* (2013.01); *G01F 1/6886* (2013.01); *G01F 1/74* (2013.01)

(58) Field of Classification Search
CPC ............. A61M 3/0204; A61M 3/0202; A61M 3/0254; A61M 5/365; A61M 2205/3368; A61M 2205/50; A61B 2018/00898; A61B 2218/002; G01F 1/6886; G01F 1/74
See application file for complete search history.

(56) References Cited

U.S. PATENT DOCUMENTS

| | | | |
|---|---|---|---|
| 4,555,940 A | 12/1985 | Renger | |
| 8,794,081 B2 | 8/2014 | Haartsen | |
| 9,445,725 B2 | 9/2016 | Govari | |
| 10,254,142 B2 | 4/2019 | Kostner | |
| 2009/0306650 A1 | 12/2009 | Govari | |
| 2010/0228222 A1 | 9/2010 | Williams | |

(Continued)

FOREIGN PATENT DOCUMENTS

| | | |
|---|---|---|
| EP | 2076137 A2 | 7/2009 |
| WO | WO2018060426 A1 | 4/2018 |

*Primary Examiner* — Laura A Bouchelle
*Assistant Examiner* — John A Doubrava (57) ABSTRACT

A method, including ejecting irrigation fluid from a distal end of a probe so as to irrigate tissue, and receiving, over a period of time, initial signals indicative of respective temperatures of the distal end, from a temperature sensor in the distal end. The method also includes formulating from the initial signals a temperature range between upper and lower temperature thresholds and, when a further signal from the temperature sensor, received subsequent to the period of time, is indicative of a further temperature above the upper temperature threshold, raising an alarm that a bubble is present in the irrigation fluid.

3 Claims, 7 Drawing Sheets

(56) References Cited

U.S. PATENT DOCUMENTS

| | | |
|---|---|---|
| 2011/0130648 A1 | 6/2011 | Beeckler |
| 2011/0308328 A1* | 12/2011 | Haartsen ............ A61M 5/16886 73/861.41 |
| 2012/0253167 A1 | 10/2012 | Bonyak |
| 2017/0273732 A1* | 9/2017 | Gutbrod ............. A61B 5/02055 |
| 2018/0238741 A1 | 8/2018 | Rud |
| 2018/0238742 A1* | 8/2018 | Basu ....................... G06F 3/147 |
| 2019/0240423 A1* | 8/2019 | O'Neill ................. A61M 5/365 |

* cited by examiner

DETECTION OF BUBBLES IN IRRIGATION FLUID

This patent application is a divisional of U.S. patent application Ser. No. 15/677,522 filed on Aug. 15, 2017.

FIELD OF THE INVENTION

The present invention relates generally to surgery, and specifically to monitoring of irrigation fluid used during the surgery.

BACKGROUND OF THE INVENTION

During some invasive medical procedures, tissue may be irrigated, and the irrigation fluid used may be monitored for the occurrence of bubbles. There are a number of aids to such monitoring that are known in the art.

U.S. Pat. No. 8,794,081, to Haartsen et al., describes a sensor for detecting bubbles in a flowing liquid. The sensor includes a heating element for heating the liquid and a transducer arrangement arranged for generating a measurement signal indicative for the temperature of the heating element. The sensor has a comparator arrangement which can generate an output signal indicative for a possible presence of bubbles in gas phase.

U.S. Pat. No. 4,555,940, to Renger, describes a system for measuring and for monitoring pulsed and steady state fluid flow through fluid flow paths. The system includes a device for modifying the temperature of part of the flow path and a device for pyroelectrically detecting changes in temperature as fluid flows through the temperature-modified part of the flow path.

U.S. Patent Application 2010/0228222, to Williams et al., describes a surgical fluid management system which may provide one or more functions associated with irrigation. The disclosure refers to different types of bubble detectors.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

ejecting irrigation fluid from a distal end of a probe so as to irrigate tissue;

receiving, over a period of time, initial signals indicative of respective temperatures of the distal end, from a temperature sensor in the distal end;

formulating from the initial signals a temperature range between upper and lower temperature thresholds; and when a further signal from the temperature sensor, received subsequent to the period of time, is indicative of a further temperature above the upper temperature threshold, raising an alarm that a bubble is present in the irrigation fluid.

In a disclosed embodiment the upper temperature threshold corresponds to a highest temperature of the respective temperatures, and the lower temperature threshold corresponds to a lowest temperature of the respective temperatures.

In a further disclosed embodiment the method includes, when the further signal from the temperature sensor is indicative of a temperature below the upper temperature threshold, adjusting the period of time to include the further signal.

In a yet further disclosed embodiment the irrigation fluid irrigates the tissue during an ablation procedure performed on the tissue.

There is further provided, according to an embodiment of the present invention, apparatus, including:

a probe having a distal end configured to eject irrigation fluid so as to irrigate tissue;

a temperature sensor located in the distal end; and a processor configured to:

receive from the temperature sensor, over a period of time, initial signals indicative of respective temperatures of the distal end, formulate from the initial signals a temperature range between upper and lower temperature thresholds, and when a further signal from the temperature sensor, received subsequent to the period of time, is indicative of a further temperature above the upper temperature threshold, raising an alarm that a bubble is present in the irrigation fluid.

There is further provided, according to an embodiment of the present invention, a method, including:

ejecting irrigation fluid from a distal end of a probe so as to irrigate tissue;

receiving, over a period of time, initial signals indicative of respective temperatures of the distal end, from a temperature sensor in the distal end;

formulating from the initial signals derivatives of the respective temperatures; and when successive derivatives cross respective preset thresholds, and occur within a predetermined time, raising an alarm that a bubble is present in the irrigation fluid.

In an alternative embodiment, the successive derivatives include a first derivative followed by a second derivative, and the preset thresholds include an upper threshold and a lower threshold, and the first derivative crosses the upper threshold when the first derivative is greater than the upper threshold, and the second derivative crosses the lower threshold when the second derivative is less than the lower threshold.

Typically, the upper threshold is within a range between 0.5° C. and 1° C., and the lower threshold is in a range between −0.5° C. and −1° C.

In a further alternative embodiment the predetermined time is within a range between 0.5 s and 1 s.

There is further provided, according to an embodiment of the present invention, apparatus, including:

a probe having a distal end configured to eject irrigation fluid so as to irrigate tissue;

a temperature sensor located in the distal end; and a processor configured to:

receive from the temperature sensor, over a period of time, initial signals indicative of respective temperatures of the distal end, formulate from the initial signals derivatives of the respective temperatures, and when successive derivatives cross respective preset thresholds, and occur within a predetermined time, raise an alarm that a bubble is present in the irrigation fluid.

The present disclosure will be more fully understood from the following detailed description of the embodiments thereof, taken together with the drawings, in which:

DETAILED DESCRIPTION OF EMBODIMENTS

Overview

There are a number of procedures, such as an ablation procedure, where tissue undergoing the procedure is irrigated. In some cases, bubbles may be created in the irrigation fluid, and if the bubbles reach the patient undergoing the procedure, it may cause safety issues. While mechanisms for detection of bubbles at an irrigation pump used to pump the irrigation fluid may exist, if the bubbles are created between the pump and a probe tip employed for the procedure, or at the probe tip, they may not be detected.

Embodiments of the present invention solve this problem by ejecting irrigation fluid from a distal end of a probe so as to irrigate tissue, and receiving, over a period of time, initial signals indicative of respective temperatures of the distal end, from a temperature sensor in the distal end. From the initial signals a temperature range between upper and lower temperature thresholds is formulated. When a further signal from the temperature sensor, received subsequent to the period of time, is indicative of a further temperature above the upper temperature threshold, an alarm is raised that a bubble is present in the irrigation fluid.

In contrast to prior art systems, embodiments of the present invention detect bubbles in the irrigation fluid at the probe distal end, and so are able to detect bubbles formed beyond the irrigation fluid pump.

System Description

In the following description, like elements in the drawings are identified by like numerals, and the like elements are differentiated as necessary by appending a letter to the identifying numeral.

Figure 1:
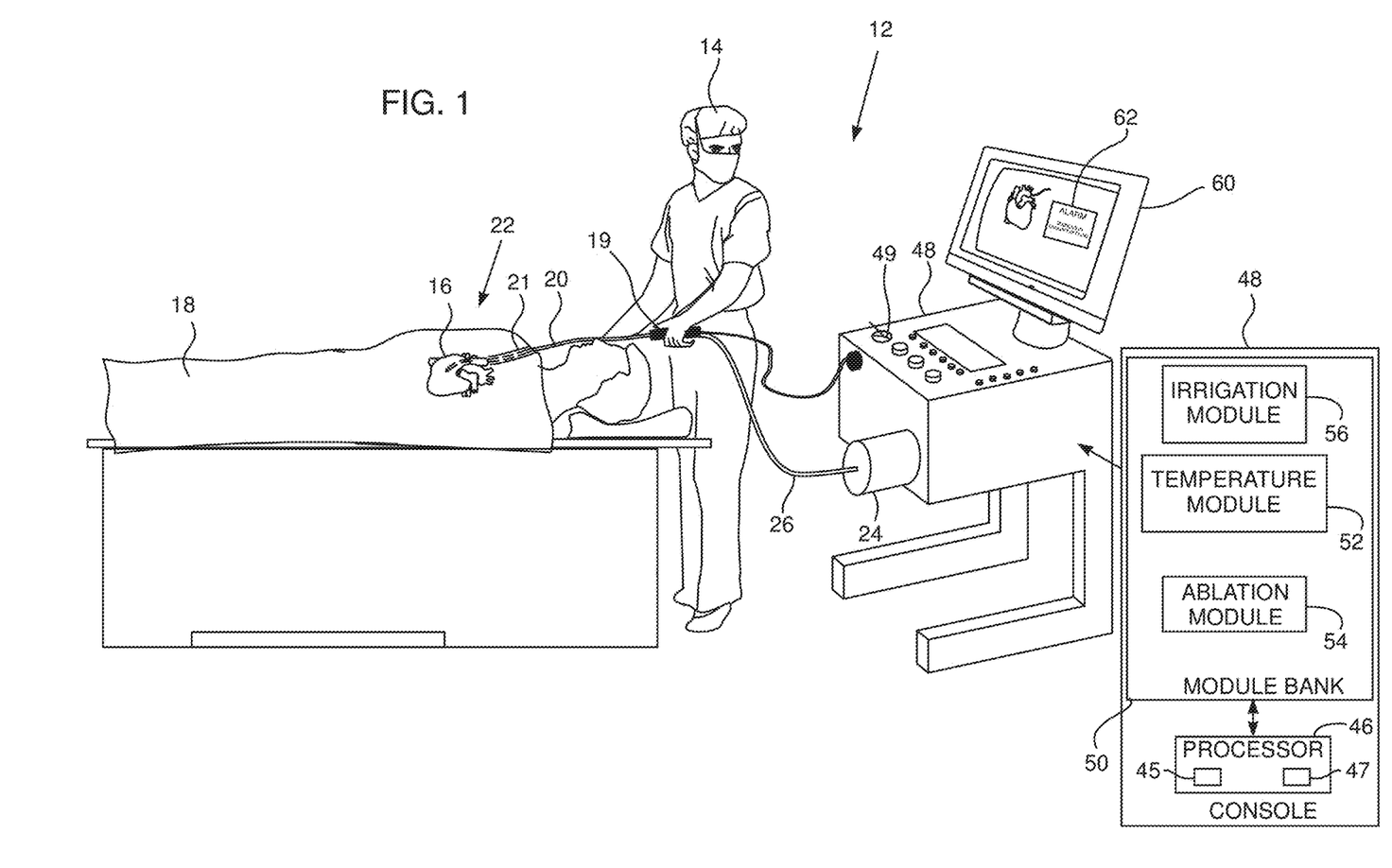
FIG. 1 is a schematic illustration of an invasive medical procedure, according to an embodiment of the present invention.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue or on non-biological material.

In order to perform the ablation, professional 14 uses a probe holder 19 to insert a probe 20 into a sheath 21 that has been pre-positioned in a lumen of the patient. Sheath 21 is positioned so that a distal end 22 of the probe may enter the heart of the patient, after exiting a distal end of the sheath, and contact tissue of the heart.

Apparatus 12 is controlled by a system processor 46 which comprises real-time noise reduction circuitry 45, typically configured as a field programmable gate array (FPGA), followed by an analog-to-digital (A/D) signal conversion integrated circuit 47. The processor can pass the signals from A/D circuit 47 to modules described herein, and/or another processor and/or can be programmed to perform at least one algorithm disclosed herein, the algorithm comprising steps described hereinbelow. The processor uses circuitry 45 and circuit 47, as well as features of the modules referred to above, in order to perform the algorithm.

Processor 46 is located in an operating console 48 of the apparatus. Console 48 comprises controls 49 which are used by professional 14 to communicate with processor 46, and to implement the procedure the processor communicates with modules in a module bank 50. The functions of modules in bank 50 are described below.

During the procedure performed by professional 14, distal end 22 is supplied with irrigation fluid, typically normal saline solution, from a pump 24. In some embodiments pump 24 comprises a peristaltic pump; alternatively any other suitable irrigation fluid pump may be used. An irrigation module 56 controls the rate of flow of the fluid from pump 24, and the pump transfers the fluid to probe 20 via irrigation tubing 26. Irrigation module 56, under overall control of processor 46, is typically configured to be able to vary the rate of fluid flow from a zero rate up to a predefined maximum rate, typically approximately 20 mL/min. In one embodiment, once distal end 22 has been inserted into sheath 21, module 56 operates pump 24 to provide a minimal fluid flow rate of approximately 5 mL/min, and the module increases this rate when professional 14 begins ablation.

Processor 46 uses a temperature module 52 to analyze signals received from temperature sensors in distal end 22. The structure and components of distal end 22, including the temperature sensors therein, are described below. From the analyzed signals, processor 46 determines temperatures of the distal end, and uses the temperatures in the algorithm described below.

Module bank 50 also comprises an ablation module 54. Ablation module 54 enables processor 46 to inject radiofrequency (RF) current, via selected electrodes of distal end 22, described below, and returning electrodes on the skin of the patient (not shown in the diagram), into myocardium 16, in order to ablate regions of the myocardium which are in contact with the selected electrodes. The ablation module also enables the processor to set parameters of the injected current, such as its frequency, the power dissipated, and the duration of the injection.

In order to operate apparatus 12, module bank 50 typically comprises modules other than those described above, such as a force module enabling the processor to measure a force on the distal end, and an electrocardiogram (ECG) module enabling the processor to acquire electropotentials from myocardium 16 via electrodes in the distal end. For simplicity, such other modules are not illustrated in FIG. 1. All modules may comprise hardware as well as software elements.

The software for processor 46 and the modules of module bank 50 may be downloaded to the processor in electronic form, over a network, for example. Alternatively or additionally, the software may be provided on non-transitory tangible media, such as optical, magnetic, or electronic storage media. The processor, and typically the modules, comprise memory used to store the downloaded software, as well as to store data generated by apparatus 12.

Processor 46 may present results of the procedure performed by professional 14, as well as results of the algorithm described below with reference to FIGS. 3 and 4, on a display screen 60.

Figure 2A:
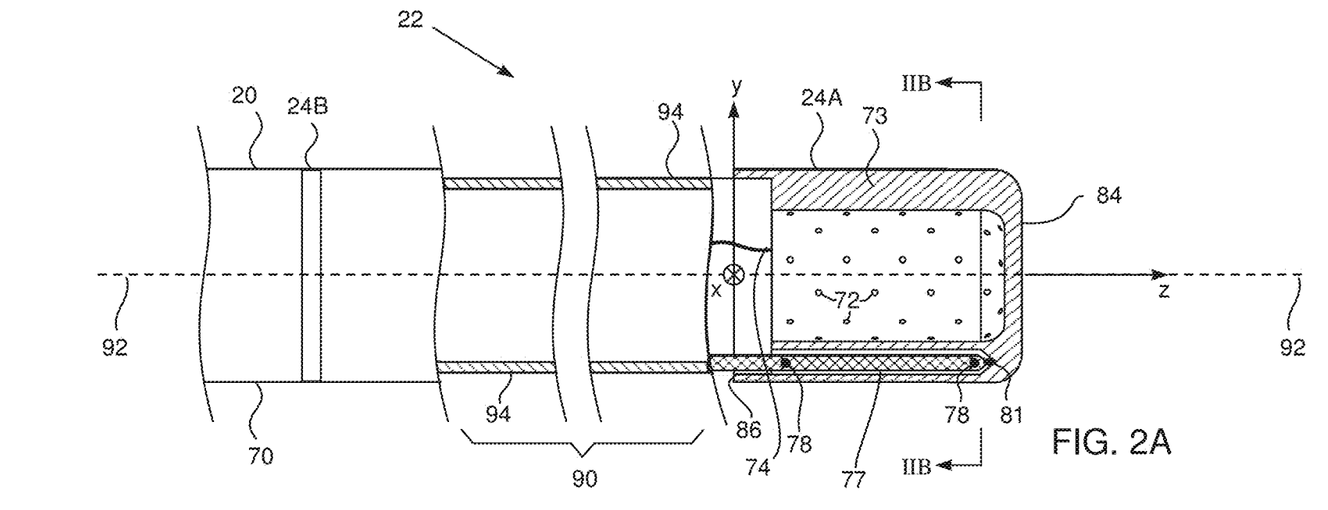
FIGS. 2A, 2B, and 2C are schematic diagrams of a distal end of a probe, according to an embodiment of the present invention.
Figure 2B:
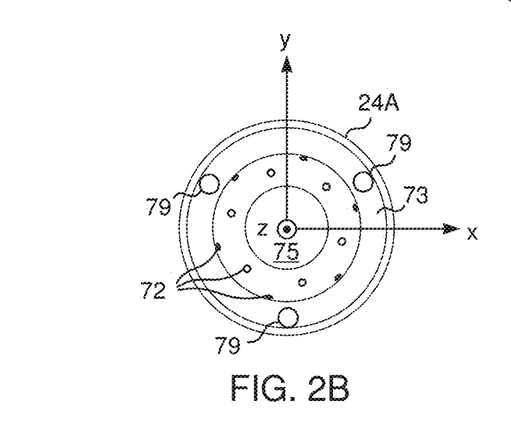
Figure 2C:
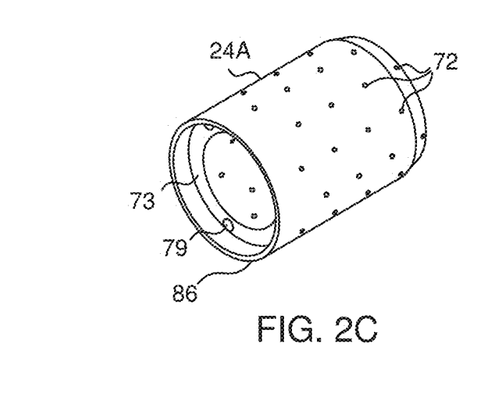

FIGS. 2A, 2B, and 2C schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, and FIG. 2C is a perspective view of a section of the distal end. An insertion tube 70 extends along the length of the probe, over a spring 94 described below, and is connected at the termination of its distal end to a conductive cap electrode 24A, which is assumed herein to be used for ablation. FIG. 2C is a schematic perspective view of cap electrode 24A. Cap electrode 24A has an approximately plane conducting surface 84 at its distal end and a substantially circular edge 86 at its proximal end. Conductive cap electrode 24A is herein also termed the ablation electrode. Proximal to ablation electrode 24A there are typically other electrodes such as electrode 24B. Typically, insertion tube 70 comprises a flexible, biocompatible polymer, while electrodes 24A, 24B comprise a biocompatible metal, such as gold or platinum, for example. Ablation electrode 24A is perforated by an array of irrigation apertures 72.

An electrical conductor 74 conveys radio-frequency (RF) electrical energy from ablation module 54 (FIG. 1), through insertion tube 70, to electrode 24A, and thus energizes the electrode to ablate myocardial tissue with which the electrode is in contact. Module 54 controls the level of RF power dissipated via electrode 24A. During the ablation procedure, irrigation fluid ejected from apertures 72, driven by pump 24, irrigates the tissue under treatment.

Temperature sensors 78 are mounted within conductive cap electrode 24A at locations that are arrayed around the distal tip of the probe, both axially and circumferentially. In this example, cap 24A contains six sensors, with one group in a distal location, close to the tip, and the other group in a slightly more proximal location. This distribution is shown only by way of example, however, and greater or smaller numbers of sensors may be mounted in any suitable locations within the cap. Sensors 78 may comprise thermocouples, thermistors, or any other suitable type of miniature temperature sensor. These sensors are connected by leads running through the length of insertion tube 70 to provide temperature signals to temperature module 52.

In a disclosed embodiment cap 24A comprises a side wall 73 that is relatively thick, on the order of 0.5 mm thick, surrounding a central cavity 75 of the tip. The irrigation fluid pumped by pump 24 enters cavity 75, and then exits the cavity through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable glue 81, such as epoxy. U.S. Pat. No. 9,445,725 to Govari et al., which is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention. Another arrangement of sensors 78 is described in U.S. Pat. No. 9,445,725 to Govari et al., referenced above.

In addition to the temperature sensors, distal end 22 typically comprises a force sensor 90 having a cylindrically shaped spring 94 which connects to side wall 73. For simplicity other elements of the force sensor are not shown in the diagram, and are not described herein. Force sensors similar to force sensor 90 are described in U.S. Patent Applications 2009/0306650 to Govari et al., 2011/0130648 to Beeckler et al., and 2012/0253167 to Bonyak et al., all of which are incorporated herein by reference.

In the description herein, distal end 22 is assumed to define a set of xyz orthogonal axes, where a symmetry axis 92 of cap 24A corresponds to the z axis of the set, and orthogonal x and y axes are in any convenient xy plane orthogonal to the z axis. For simplicity, the xy plane is herein assumed to correspond to the plane defined by circle 86, and the origin of the xyz axes is assumed to be the center of the circle.

Typically, distal end 22 contains other functional components, which are outside the scope of the present disclosure, so that further references to them are therefore omitted for the sake of simplicity. For example, the distal end of the probe may contain steering wires, as well as sensors of other types, such as a position sensor. Probes containing components of these kinds are described, for example, in U.S. Patent Applications 2009/0306650 and 2011/0130648, referenced above.

First Embodiment

Figure 3:
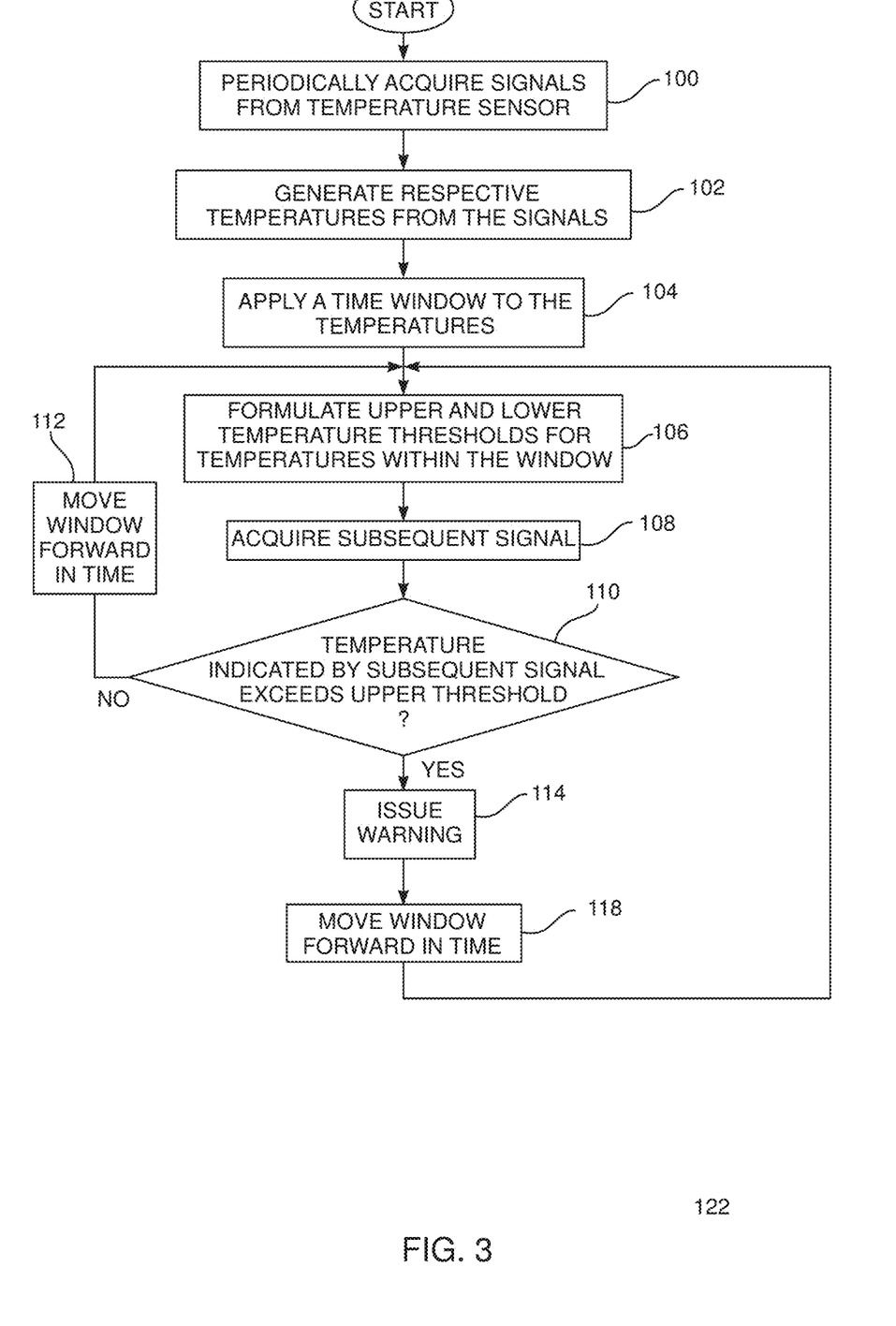
FIG. 3 is a flowchart of steps of an algorithm performed during the procedure, according to an embodiment of the present invention.
Figure 4:
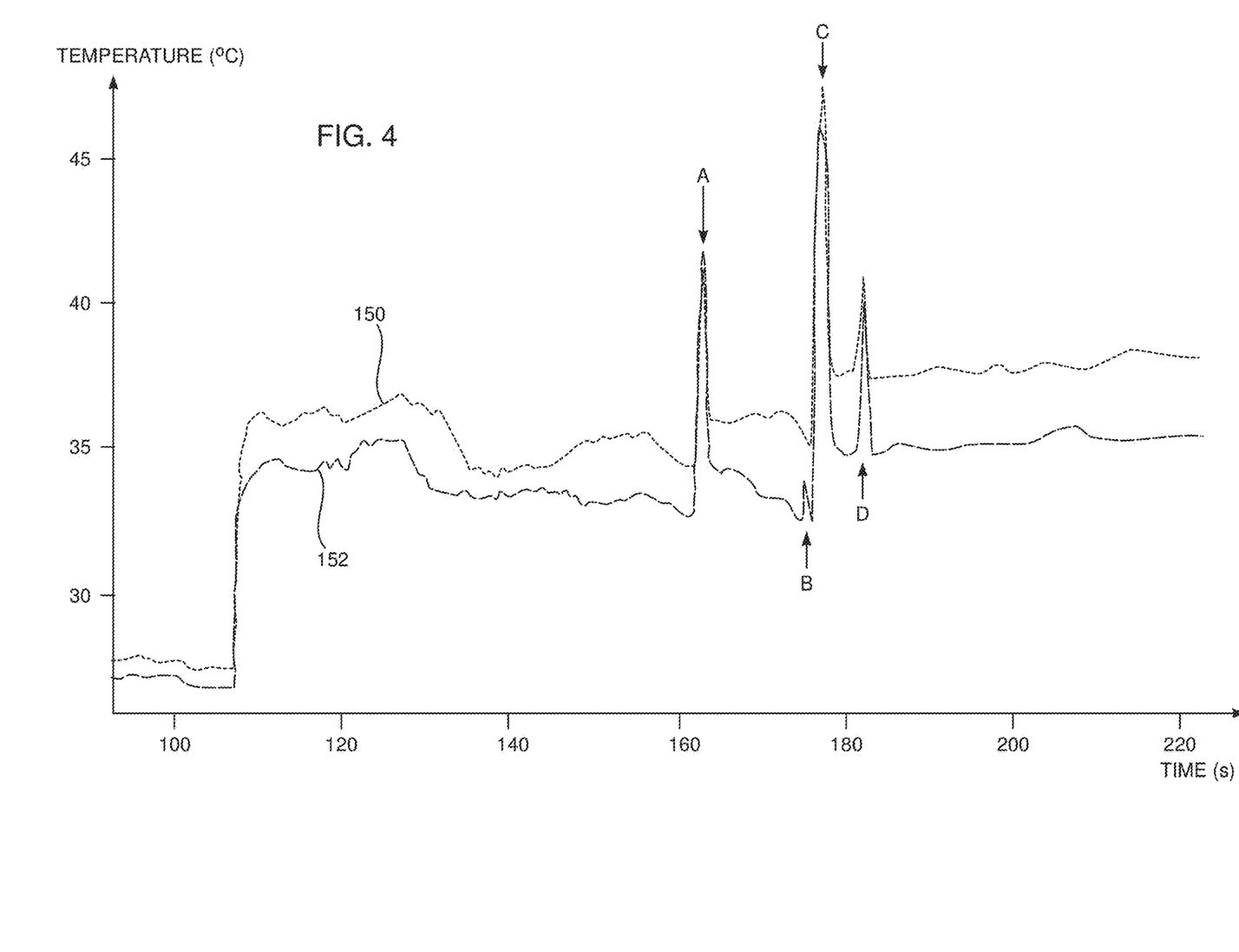
FIG. 4 is a schematic graph illustrating results acquired during operation of the algorithm, according to an embodiment of the present invention.

FIG. 3 is a flowchart of steps performed by processor 46 in implementing the algorithm referred to above, and FIG. 4 shows schematic graphs illustrating some of the steps, according to an embodiment of the present invention. The flowchart of FIG. 3 describes actions performed by the processor in analyzing signals from a single temperature sensor 78, herein for clarity referred to as sensor 78A, in distal end 22. As is stated above, embodiments of the present invention may have one or more temperature sensors in the distal end, and in the case of more than one sensor the processor typically applies the actions of the flowchart to the signals from each of the sensors simultaneously.

In an initial step 100 of the flowchart, the processor periodically acquires signals from sensor 78A on a continuing basis. Typically, signals are acquired with a sample period of approximately 50 ms, although the rates of signal acquisition may be in a range of 10 ms-100 ms, or may be higher or lower than this range.

In a temperature generation step 102, the processor digitizes and reduces noise on the signals, as described above. In some embodiments the noise reduction includes passing the signals through one or more of a low pass filter, typically with a cut off of 1-5 Hz, (the low pass filter may be a median filter), and a high pass filter with a typical cut off of 0.1 Hz. The processor uses temperature module 52 to convert the signals to temperatures, and the processor stores the temperatures calculated in the step. The graphs of FIG. 4 plot temperature vs. time, and a graph 150 schematically illustrates the varying temperature with time of sensor 78A. A graph 152 schematically illustrates the varying temperature with time of another distal end sensor 78, herein referred to as sensor 78B. Graphs 150 and 152 are generated from a simulation of apparatus 12.

In a windowing step 104, the processor selects the most recent group of temperatures that have been acquired within a preset period of time, herein also termed a window of time. In one embodiment the preset window of time is 1 second, but in other embodiments the preset window may be longer or shorter than this period of time.

In an analysis step 106, the processor uses the acquired temperature values to formulate an upper and a lower threshold value for the windowed temperatures, herein respectively also termed an upper temperature $T_u$ and a lower temperature $T_l$. The processor also computes and stores a range $\Delta T$, herein termed the window range, indicative of the temperature difference between the upper and lower temperatures. Equation (1) below gives an expression for $\Delta T$.

$$\Delta T = T_u - T_l \qquad (1)$$

where $T_u$ is the highest temperature in the window,
$T_l$ is the lowest temperature in the window, and
$\Delta T$ is the temperature range in the window.

In some embodiments, rather than calculating upper and lower threshold values, the processor fits a median line, typically a straight line of temperatures vs. time, to the windowed temperatures. The processor then formulates the upper temperature and lower temperature as upper and lower lines parallel to the median line. Where a median line is used, the window range is computed as a range between the upper and lower lines.

A typical value for the temperature difference, i.e., the window range $\Delta T$, in a window of 1 second is 1° C.

In a first acquisition step 108, the processor acquires a further signal, after the preset window of time, from sensor 78A, and calculates the temperature indicated by the further signal.

In a comparison step 110, the processor compares the temperature calculated in step 108 with the upper threshold value calculated in analysis step 106. Alternatively, if in step 106 the processor calculates the upper temperature and the lower temperature as upper and lower lines, the processor compares the temperature calculated in step 108 with an upper threshold value calculated by extrapolating the upper line.

If comparison step 110 returns a negative value, i.e., the temperature measured in step 108 is below the upper threshold, control of the algorithm continues to a first move window step 112. In the move window step the processor advances the preset time window, typically by one sample period, and control of the flowchart returns to step 106.

If comparison step 110 returns a positive value, i.e., the temperature measured in step 108 is above the upper threshold, then it is assumed that the increase in temperature is caused by a bubble in the irrigation fluid. In this case control of the algorithm continues to an issue warning step 114, wherein the processor raises an alarm of the presence of bubbles in the irrigation fluid to professional 14. The alarm may be an auditory non-verbal warning, such as a ring, or a recorded statement, that is broadcast to the professional. Alternatively or additionally, the alarm may be a visual warning, such as a light that is switched on, or a warning notice 62 that is placed on screen 60. Further alternatively or additionally, the alarm may be a tactile warning, such as by vibrating probe holder 19.

After step 114 control of the algorithm proceeds to a second move window step 118, which is substantially the same as step 112. I.e., in the second move window step the processor advances the preset time window, typically by one sample period. After step 118, control of the algorithm returns to analysis step 106.

The alarm of step 114 is typically presented for a preset period of time, for example 2 seconds, after which the alarm is switched off. In some embodiments the alarm is only raised after comparison step 110 has returned more than a preset number N of positive values, where N is 2 or more. In some embodiments professional 14 may clear the alarm and return the flowchart to analysis step 106.

As stated above, processor 46 typically implements the algorithm represented by the flowchart of FIG. 3 for each temperature sensor 78 substantially simultaneously, and the alarm of the presence of bubbles is raised if control of any one of the algorithms passes to issue warning step 114. Alternatively, the alarm of the presence of bubbles may be raised if control of a preset number, typically two or more, of the algorithms for respective sensors 78 passes to warning step 114.

The temperature vs. time graphs of FIG. 4 illustrate times A, B, C, and D at which bubbles are identified by the flowchart of FIG. 3. As is illustrated by the graphs, at the times of occurrence of the bubbles, A, B, C, and D, there are sharp peaks in the graphs. These peaks are identified by first comparison 110 of the flowchart returning positive.

Second Embodiment

Figure 5:
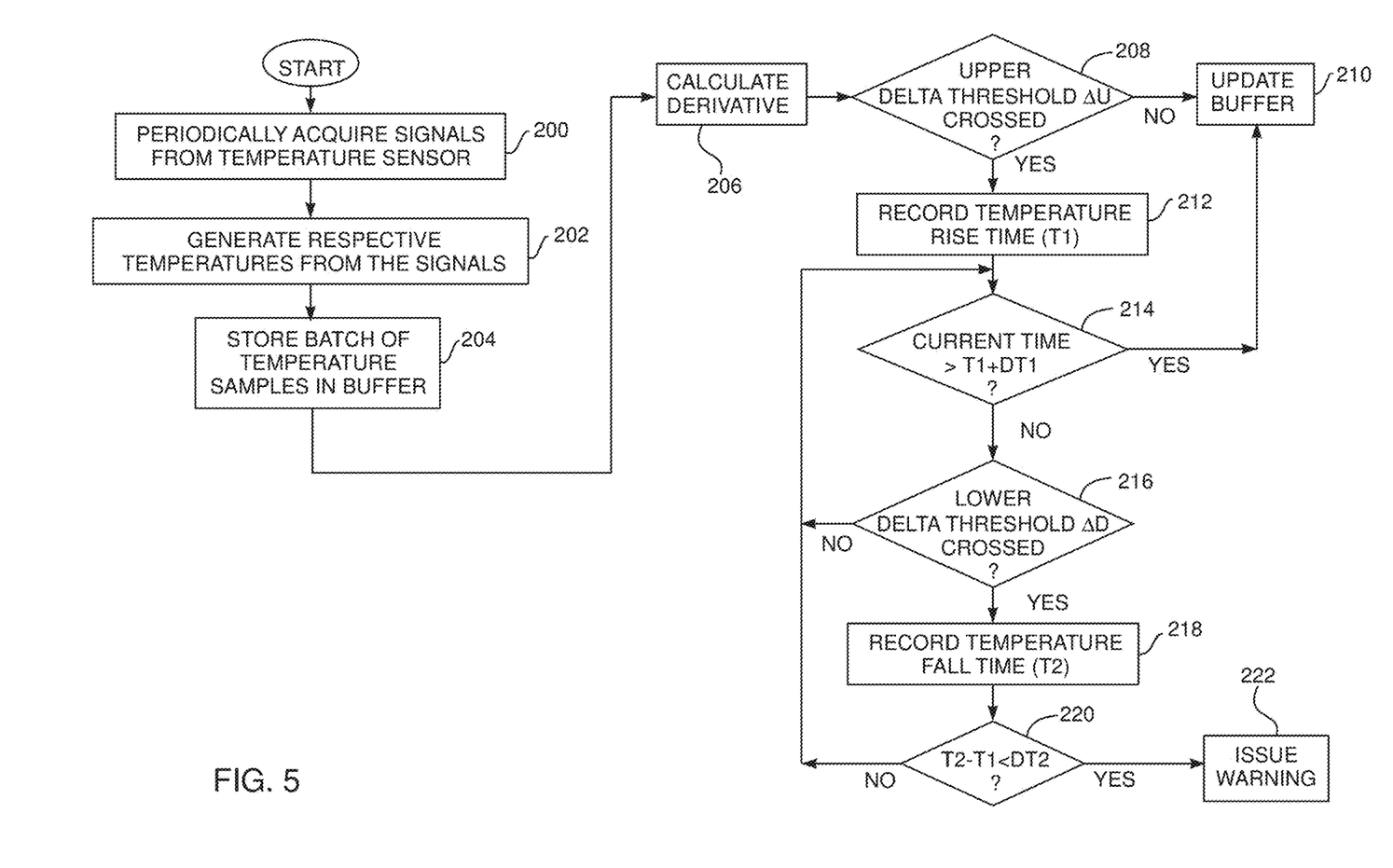
FIG. 5 is a flowchart of steps of an algorithm performed during the procedure, according to an alternative embodiment of the present invention.
Figure 6:
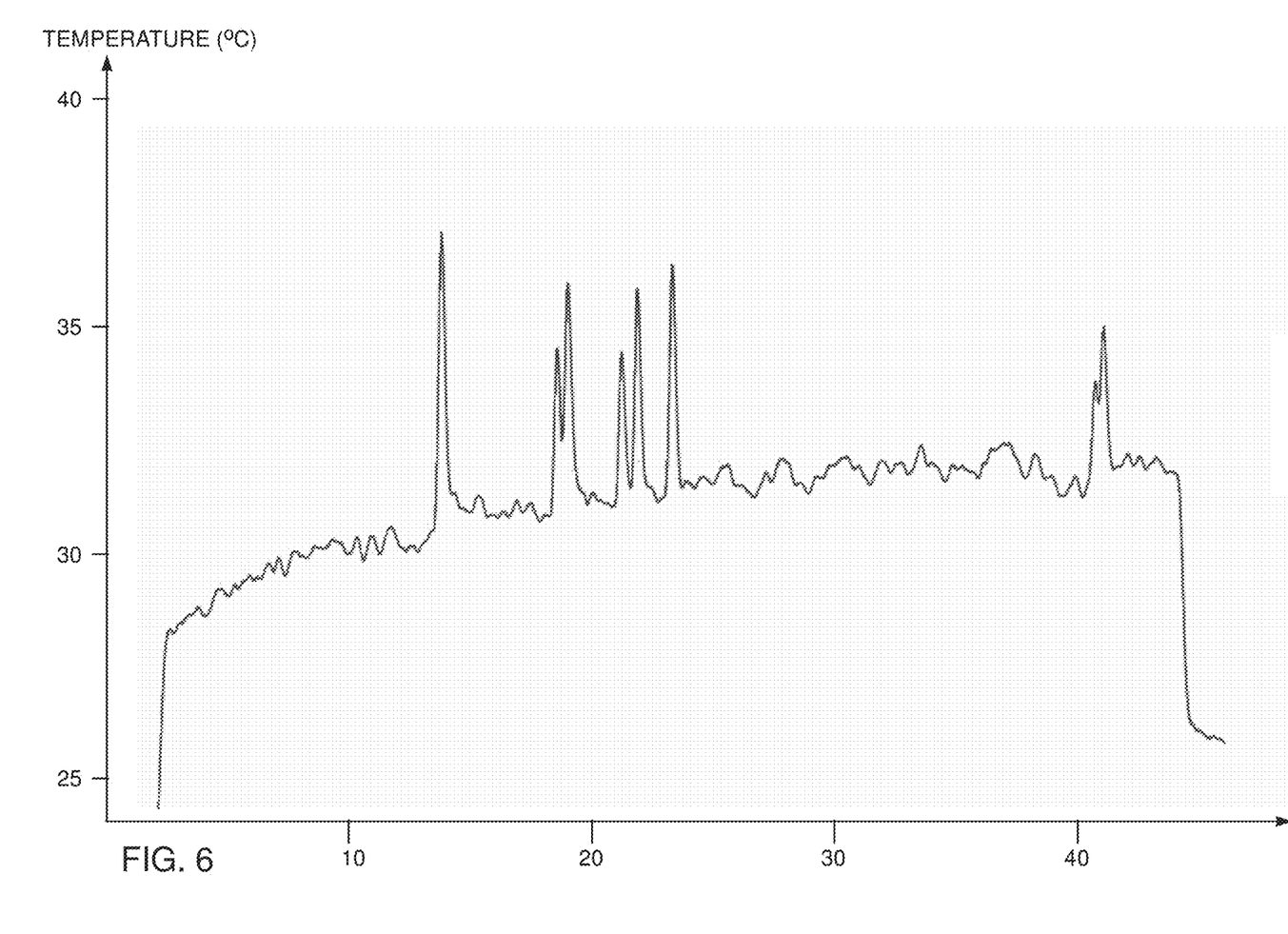
FIGS. 6 and 7 show schematic graphs illustrating some of the steps of the flowchart of FIG. 5.
Figure 7:
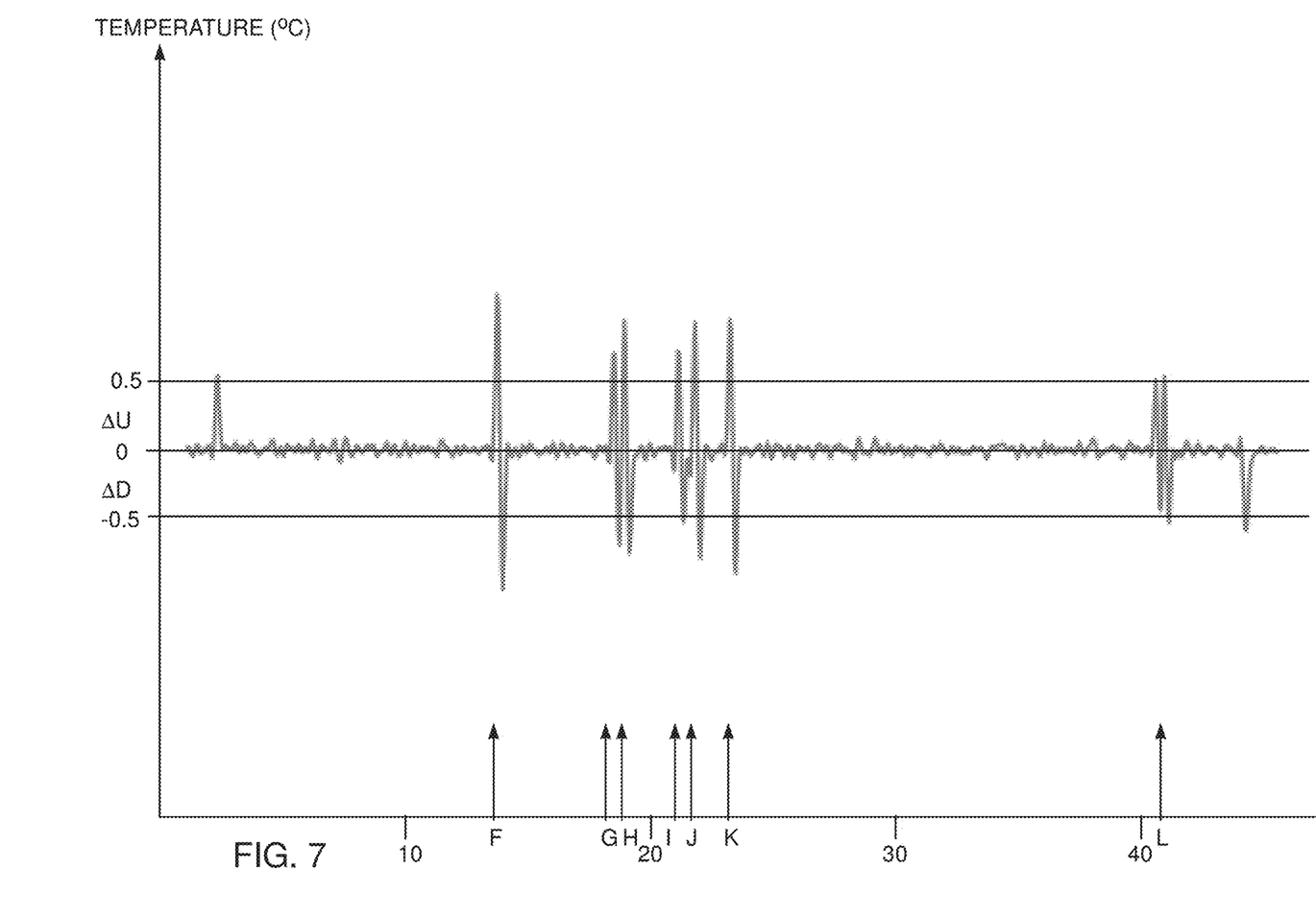

FIG. 5 is a flowchart of steps performed by processor 46 in implementing the algorithm referred to above, and FIGS. 6 and 7 show schematic graphs illustrating some of the steps, according to an alternative embodiment of the present invention. As for the flowchart of FIG. 3, the flowchart of FIG. 5 describes actions performed by the processor in analyzing signals from a single temperature sensor 78, herein for clarity referred to as sensor 78A, in distal end 22. In the case of more than one sensor the processor typically applies the actions of the flowchart to the signals from each of the sensors simultaneously.

The actions performed by the processor in an initial step 200, and a temperature generation step 202 are respectively substantially as described above for steps 100 and 102 (FIG. 3).

In a store sample step 204, processor 46 stores a batch of temperature samples to be analyzed in a moving buffer of samples, and the processor updates the buffer as described below.

In a derivative step 206 the processor calculates the derivative of the first sample in the buffer, typically by finding the difference between the temperature value of the first sample, and the temperature value of one or more preceding samples in the buffer.

In a first comparison 208, the processor checks if the derivative is greater than a preset upper delta threshold $\Delta U$, i.e., if the threshold has been crossed. $\Delta U$ is typically set to be between 0.5° C. and 1° C. If the comparison returns negative, i.e., the threshold has not been crossed, then the processor assumes that the sampled group does not indicate the presence of a bubble. In this case control proceeds to an update buffer step 210 where the processor updates the buffer of step 204, typically by introducing a new sample from generation step 202 to the end of the buffer, while removing the sample used in the analysis in comparison 208 from the buffer.

If the first comparison returns positive, then in a time recordation step 212 the processor records the time T1 at which the threshold ΔU is crossed.

In the following steps of the flowchart, the processor analyzes the remaining samples in the buffer to determine whether or not the positive return of comparison 208 is indicative of the presence of a bubble.

Thus, in a second comparison 214, the processor checks if the time between T1 and the time of the sample being analyzed is greater than a preset time delta DT1, which is typically set to be within a range between 0.5 s and 1 s.

If comparison 214 returns positive, then the processor assumes that the threshold crossing of comparison 208 is not due to a bubble, since embodiments of the present invention assume that a bubble causes upper and lower thresholds, ΔU and ΔD, to both be crossed within a preset time period DT2. (ΔU and ΔD are illustrated in FIG. 7, where by way of example they are set as +0.5° C. and −0.5° C.) DT2 is typically set within a range between 0.5 s and 1 s. Typical cases where comparison 214 returns positive are at the beginning of an ablation procedure (where there is a sharp rise of temperature) or a movement of the temperature sensor. After comparison 214 returns positive, control continues at update buffer step 210.

If comparison 214 returns negative, the processor proceeds to a third comparison 216, where the processor checks if the derivative associated with the sample being analyzed crosses a preset lower delta threshold ΔD, i.e., if the analyzed derivative is less than the preset lower delta threshold ΔD. ΔD is typically set to be between −0.5° C. and −1° C.

If comparison 216 returns negative, i.e., the lower threshold has not been crossed, then control returns to comparison 214, where the processor checks a subsequent sample in the buffer.

If comparison 216 returns positive, so that the lower threshold has been crossed, then in a recordation step 218 the processor records a time T2 associated with the sample being analyzed. The processor then checks in a final comparison 220 if the time difference 12-T1 is less than preset time period DT2.

If comparison 220 returns positive the processor assumes that the temperature changes of the analyzed samples are due to a bubble, and in a raise alarm step 222 the processor issues a warning.

If comparison 220 returns negative the processor assumes that the temperature changes of the analyzed samples are not due to a bubble, and control returns to comparison 214, where the processor checks a subsequent sample in the buffer.

FIG. 6 is a temperature vs. time graph, illustrating temperatures, after they have been filtered, and that are analyzed according to the flowchart of FIG. 5. FIG. 7 is a graph of the derivatives of the temperatures that are used by the flowchart, and exemplary values of upper and lower delta thresholds, ΔU and UD, have been drawn on the graph as +0.5° C. and −0.5° C. As is illustrated, at times F, G, H, . . . L, both thresholds are crossed within a short time of each other, so that comparison 222 (FIG. 5) returns positive, indicating the presence of a bubble, and the processor raises a warning.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus, comprising:
a probe having a distal end configured to eject irrigation fluid so as to irrigate tissue;
a temperature sensor located in the distal end; and
a processor configured to:
receive from the temperature sensor, over a period of time, initial signals indicative of respective temperatures of the distal end,
formulate from the initial signals derivatives of the respective temperatures, and
when successive derivatives cross respective preset thresholds, and occur within a predetermined time, raise an alarm that a bubble is present in the irrigation fluid; wherein the successive derivatives comprise a first derivative followed by a second derivative, and wherein the preset thresholds comprise an upper threshold and a lower threshold, and wherein the first derivative crosses the upper threshold when the first derivative is greater than the upper threshold, and wherein the second derivative crosses the lower threshold when the second derivative is less than the lower threshold.

2. The apparatus according to claim 1, wherein the upper threshold is within a range between 0.5° C. and 1° C., and the lower threshold is in a range between −0.5° C. and −1° C.

3. The apparatus according to claim 1, wherein the predetermined time is within a range between 0.5 s and 1 s.

* * * * *